US012673285B2

(12) United States Patent
Mani et al.

(10) Patent No.: US 12,673,285 B2
(45) Date of Patent: Jul. 7, 2026

(54) AIR PURIFIER

(71) Applicant: BISSELL, INC., Grand Rapids, MI (US)

(72) Inventors: Deepa Mani, South Lyon, MI (US); Victoria J. Royale, Comstock Park, MI (US); Mackenzie Leigh Knapp, Saranac, MI (US); Todd W. Duell, Sodus, MI (US)

(73) Assignee: BISSELL Inc., Grand Rapids, MI (US)

( * ) Notice: Subject to any disclaimer, the term of this patent is extended or adjusted under 35 U.S.C. 154(b) by 318 days.

(21) Appl. No.: 18/467,881

(22) Filed: Sep. 15, 2023

(65) Prior Publication Data

US 2024/0017195 A1 Jan. 18, 2024

Related U.S. Application Data

(63) Continuation of application No. PCT/US2022/017468, filed on Feb. 23, 2022.
(Continued)

(51) Int. Cl.
B01D 46/00 (2022.01)
A61L 2/10 (2006.01)
(Continued)

(52) U.S. Cl.
CPC ............ B01D 46/0004 (2013.01); A61L 2/10 (2013.01); A61L 9/20 (2013.01); B01D 46/0005 (2013.01); B01D 46/0006 (2013.01); B01D 46/0027 (2013.01); B01D 46/0028 (2013.01); B01D 46/0084 (2013.01); B01D 46/009 (2013.01); B01D 46/4245 (2013.01); F24F 8/22 (2021.01); A61L 2202/11

(2013.01); *A61L 2202/122* (2013.01); *A61L 2202/14* (2013.01); *A61L 2209/11* (2013.01); *A61L 2209/111* (2013.01);
(Continued)

(58) Field of Classification Search
CPC ................ B01D 46/00; B01D 46/0005; B01D 46/0006; B01D 46/0027; B01D 46/0084
See application file for complete search history.

(56) References Cited

U.S. PATENT DOCUMENTS 6,464,760 B1 10/2002 Sham
6,783,578 B2 8/2004 Tillman, Jr.
(Continued)

FOREIGN PATENT DOCUMENTS

CN 212644878 U * 3/2021
CN 212777778 U 3/2021
(Continued)

OTHER PUBLICATIONS

Molekule, available at https://web.archive.org/web/20201108111846/https://molekule.com/technology, available at least as early as Nov. 8, 2020, 3 pages.
(Continued)

*Primary Examiner* — Robert A Hopkins
(74) *Attorney, Agent, or Firm* — McGarry Bair PC

(57) ABSTRACT

An air purifier for inside air. The air purifier includes a housing and a closure assembly. The closure assembly is slideably and selectively removable from the housing. The closure assembly includes a cage on which a filter can be mounted. One or more sensors can detect the location of the closure assembly relative to the housing.

20 Claims, 8 Drawing Sheets

Related U.S. Application Data

(60) Provisional application No. 63/163,242, filed on Mar. 19, 2021.

(51) Int. Cl.

| | |
|---|---|
| *A61L 9/20* | (2006.01) |
| *B01D 46/42* | (2006.01) |
| *F24F 8/22* | (2021.01) |

(52) U.S. Cl.

CPC ....... *A61L 2209/14* (2013.01); *B01D 2279/50* (2013.01); *B01D 2279/65* (2013.01)

(56) References Cited

U.S. PATENT DOCUMENTS

| | | | |
|---|---|---|---|
| 7,530,140 | B2 | 5/2009 | Makarov |
| D658,751 | S | 5/2012 | Farone |
| D658,752 | S | 5/2012 | Farone |
| D716,428 | S | 10/2014 | Farone |
| D731,633 | S | 6/2015 | Farone |
| D745,128 | S | 12/2015 | Farone |
| D751,184 | S | 3/2016 | Farone |
| D829,312 | S | 9/2018 | Riering-Czekalla |
| 10,137,216 | B2 | 11/2018 | Goswami |
| 10,584,886 | B2 | 3/2020 | Goswami |
| 10,625,207 | B2 | 4/2020 | Rao |
| 10,684,027 | B2 | 6/2020 | Goswami |
| D890,904 | S | 7/2020 | Farone |
| D890,905 | S | 7/2020 | Farone |
| 10,842,907 | B2 | 11/2020 | Goswami |
| D905,220 | S | 12/2020 | Farone |
| 2004/0020363 | A1 | 2/2004 | Laferriere et al. |
| 2008/0148696 | A1 | 6/2008 | Niedermann |
| 2010/0000413 | A1 | 1/2010 | Turner |
| 2010/0095844 | A1 | 4/2010 | Gilleland |
| 2017/0348455 | A1 | 12/2017 | Kim |
| 2020/0030731 | A1 | 1/2020 | Dhau |
| 2020/0166225 | A1 | 5/2020 | Goswami |
| 2020/0222576 | A1 | 7/2020 | Goswami |
| 2020/0271335 | A1 | 8/2020 | Goswami |
| 2020/0363081 | A1 | 11/2020 | Park |
| 2021/0030916 | A1 | 2/2021 | Goswami |

FOREIGN PATENT DOCUMENTS

| | | |
|---|---|---|
| JP | 6597891 B2 | 10/2019 |
| JP | 2020071017 A | 5/2020 |
| KR | 100565775 B1 | 3/2006 |
| KR | 1020170051200 A | 5/2017 |

OTHER PUBLICATIONS

Guardian AC9200WCA, available at https://guardiantechnologies. com/products/germguardian-ac9200wca-large-room-allergen-and-odor-reducing-air-purifier, available at least as early as Mar. 4, 2021, 2 pages.

Guardian AC5900WCA, available at https://www.guardiantechnologies. com/collections/air-purifiers-with-uv-hepa-filters/products/air-purifiers-with-uv-hepa-filters-ac5900wca-true-hepa-ultra-quiet-air-purifier-system-with-uv-c-allergy-and-odor-reduction-mid-size-console, available at least as early as Mar. 4, 2021, 3 pages.

Guardian AC4825, available at https://guardiantechnologies.com/ products/germguardian-ac4825-4-in-1-air-purifier-with-hepa-filter-uvc-sanitizer-and-odor-reduction-22-inch-tower-black, available at least as early as Mar. 4, 2021, 3 pages.

* cited by examiner

AIR PURIFIER

CROSS REFERENCE TO RELATED APPLICATION(S)

This application is a continuation of International Application No. PCT/US2022/017468, filed Feb. 23, 2022, which claims the benefit of Provisional Application No. 63/163, 242, filed Mar. 19, 2021, all of which are incorporated herein by reference in their entirety.

BACKGROUND

Air purifying devices filter particles from inside air and/or kill airborne pathogens. Such devices typically use filters or ion injectors to purify the air surrounding the device. Yet there are continual issues in manufacture, operation, function, and ornamental appearance that remain unresolved.

BRIEF DESCRIPTION

An air purifier comprising a housing defining an interior, the housing having an opening, a closure assembly selectively moveable between a closed position and an opened position, wherein the closure assembly in the closed position at least partially closes the opening, the closure assembly further comprising a filter mount, and a bulb mount configured to retain a light source and wherein power is unavailable to the light source if the closure assembly is in an at least partially opened position.

DETAILED DESCRIPTION

Figure 1:
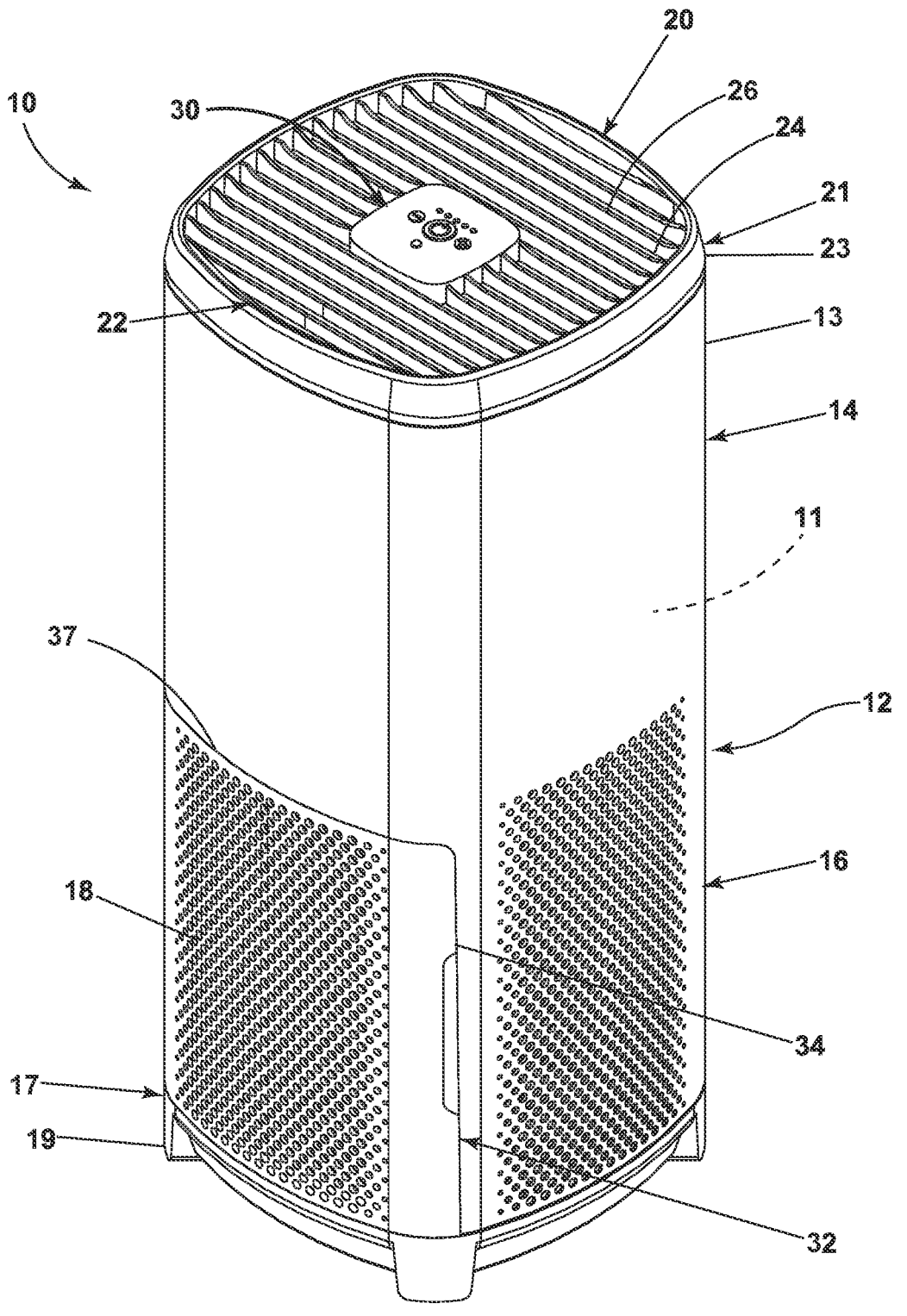
FIG. 1 is a perspective view of an air purifier with a closure assembly in a closed position defined by a first position according to various aspects described herein.

Aspects of the disclosure relate to an air purifier apparatus. The term "clean" as used herein is to describe the removal of dust, dirt, contaminates, or other particles from air as compared to the ambient air. The term "purify" is used herein to describe killing or inactivating pathogens or microorganisms in the ambient air. It is noted that the air purifier apparatus can have a variety of applications including both commercial or home based.

As used herein, the term "upstream" refers to a direction that is opposite the air flow direction, and the term "downstream" refers to a direction that is in the same direction as the air flow. Additionally, as used herein, the terms "radial" or "radially" refer to a direction away from a common center. Furthermore, as used herein, the term "set" or a "set" of elements can be any number of elements, including only one.

All directional references (e.g., radial, axial, proximal, distal, upper, lower, upward, downward, left, right, lateral, front, back, top, bottom, above, below, vertical, horizontal, clockwise, counterclockwise, upstream, downstream, etc.) are only used for identification purposes to aid the reader's understanding of the present disclosure, and do not create limitations, particularly as to the position, orientation, or use of aspects of the disclosure described herein. Connection references (e.g., attached, coupled, secured, fastened, connected, and joined) are to be construed broadly and can include intermediate members between a collection of elements and relative movement between elements unless otherwise indicated. As such, connection references do not necessarily infer that two elements are directly connected and in fixed relation to one another. The exemplary drawings are for purposes of illustration only and the dimensions, positions, order and relative sizes reflected in the drawings attached hereto can vary.

Additionally, as used herein, a "controller" can include a component configured or adapted to provide instruction, control, operation, or any form of communication for operable components to effect the operation thereof. A controller module can include any known processor, microcontroller, or logic device. Non-limiting examples of a controller can be configured or adapted to run, operate, or otherwise execute program code to effect operational or functional outcomes, including carrying out various methods, functionality, processing tasks, calculations, comparisons, sensing or measuring of values, or the like, to enable or achieve the technical operations or operations described herein. In another non-limiting example, a controller can also include a data storage component accessible by the processor, including memory, whether transient, volatile or non-transient, or non-volatile memory. Additional non-limiting examples of the memory can include Random Access Memory (RAM), Read-Only Memory (ROM), flash memory, or one or more different types of portable electronic memory, such as discs, DVDs, CD-ROMs, flash drives, universal serial bus (USB) drives, the like, or any suitable combination of these types of memory. In one example, the program code can be stored within the memory in a machine-readable format accessible by the processor. Additionally, the memory can store various data, data types, sensed or measured data values, inputs, generated or processed data, or the like, accessible by the processor in providing instruction, control, or operation to effect a functional or operable outcome, as described herein.

Additionally, as used herein, elements being "electrically connected," "electrically coupled," or "in signal communication" can include an electric transmission or signal being sent, received, or communicated to or from such connected or coupled elements. Furthermore, such electrical connections or couplings can include a wired or wireless connection, or a combination thereof.

The term "monolithic body" as used herein means a single body that is a single, non-separable piece, or formed as a single unitary piece at manufacture, as opposed to being formed by combining separate elements into one during manufacture. The term "squircle" as used herein is a shape intermediate between a square and a circle.

FIG. 1 illustrates an air purifier 10 including a housing 12. The air purifier 10 can be a standalone air purifier. That is, the air purifier 10 can a standalone or single unit that is separate from and not included in whole house or building systems such as a heating system, ventilation system, or air conditioning system, nor it is included in a furniture article.

An interior 11 of the air purifier 10 can at least partially be defined by the housing 12. The housing 12 defines an exterior periphery 13 for the air purifier 10. The housing 12 can further define an upper portion 14 and a lower portion 16. The upper portion 14 and the lower portion 16 can divide the housing 12 in half vertically. However, it is contemplated that the upper portion 14 can be greater than or less than half of the housing 12, with the lower portion 16 defining the remaining portion of the housing 12. The lower portion 16 can include a bottom portion or a base 17. Optionally, the base 17 can include feet, legs 19, or other supporting structures.

The housing 12 can be a monolithic body. Alternatively, the housing 12 can be defined by more than one component coupled together. The shape of the housing 12, as illustrated by way of example is a prism, having a base or cross-sectional shape that is a squircle, however it is contemplated that the housing 12 can be any shape, such as, but not limited to, a cylinder having a base or cross-sectional shape that is a circle, a round rectangular prism having a base or cross-sectional shape that is a rounded rectangle, a cube-like shape with a cross section that is square, or an elliptic cylinder having a cross-sectional shape that is an ellipse or oval.

By way of non-limiting example, the lower portion 16 has been illustrated as including a plurality of perforations 18 on multiple sides of the housing 12. It is contemplated that the plurality of perforations 18 can be included on any number of sides of the housing 12 including on only a single side. Further, while the plurality of perforations 18 have been illustrated as being generally uniform in shape and size, it is contemplated that the plurality of perforations 18 can be perforations of different shapes and sizes.

A top portion 20 of the housing is illustrated as being provided adjacent the upper portion 14. A lip or ledge 21 can define a perimeter of the top portion 20. The ledge 21 can be uniformly formed with the housing 12 or be a separate component of the housing 12. The lip or ledge 21 can include a channel or recess 23 configured to receive an accessory device. A magnetic rail located at or included in the lip or ledge 21 can be configured to receive an accessory or an accessory device. The ledge 21 or recess 23 can also be configured to supply power to an accessory device.

It is contemplated that the ledge 21 or recess 23 can receive, by way of non-limiting example, a tabletop accessory, a filter accessory, an air freshener or scent accessory, a humidification accessory. Any accessory device is contemplated, where the accessory device is configured to operate or function independently from the air purifier 10 or complementarily to the air purifier 10. When operating complimentary to the air purifier 10 the accessory device will not operate unless the air purifier 10 or a cycle of operation for the air purifier is selected. Independently operating accessory devices can be activated or deactivated regardless of the operating state of the air purifier 10. However, it is contemplated that while operating independently, the independently operating accessory device can be automatically activated based on recognition of at least a portion of a cycle of operation of the air purifier 10. Further, a static, inert, or non-powered accessory device can be considered independent, as the presence of such an accessory device does not depend on the operation of the air purifier 10.

In the illustrated example, and by way of non-limiting example, the top portion 20 has a similar shape to a cross-section of the housing 12. That is, the top portion 20 is generally shaped as a squircle, although this need not be the case. That is, the housing 12 can have a cross-section similar in shape to the top portion 20, alternatively, the top portion 20 can have a different shape or be a different size than a cross-section of the housing 12. A vent 22 can be provided within the top portion 20. The vent 22 can include a body defining a plurality of flow divertors 26, which define a plurality of openings 24 defined therebetween. While illustrated as generally parallel beams or beams that extend in the same direction, the flow divertors 26 can be any shape, size, profile, spacing, or orientation. Further, the flow divertors 26 can be defined by two or more pieces or components.

A user interface 30 can be provided with the top portion 20 of the housing 12. More specifically, the user interface 30 can be located at an upper surface of the air purifier, although this need not be the case and the user interface 30 can be provided at any suitable location. It is contemplated, however, that the user interface 30 can be located on one or more sides of the housing 12. In the non-limiting illustrated example, the user interface 30 can be operably coupled to the housing 12. That is, the user interface 30, by way of non-limiting example, can be mounted to or formed with the housing 12. Further still, while a single user interface 30 is shown, it is further contemplated that the air purifier 10 can include more than one user interface. Optionally, the air purifier 10 can be remotely controlled by one or more electronic devices such as, but not limited to, a handheld remote or a cellular phone.

A closure assembly 32 can be movably mounted to the air purifier 10 for movement between a closed position defined by a first position and an opened position or partially opened position defined by a second position. A face 34 of the closure assembly 32 defines at least a portion of the housing 12 when the closure assembly 32 is in the first position. As illustrated in FIG. 1, by way of non-limiting example, the closure assembly 32 is in the closed position as defined by the first position when the face 34 of the closure assembly 32 aligns with at least a portion of one of the sides of the housing 12. That is, the closure assembly 32 is in the closed position as defined by the first position when an opening 37 in the housing 12 receives the face 34 of the closure assembly 32.

Figure 2:
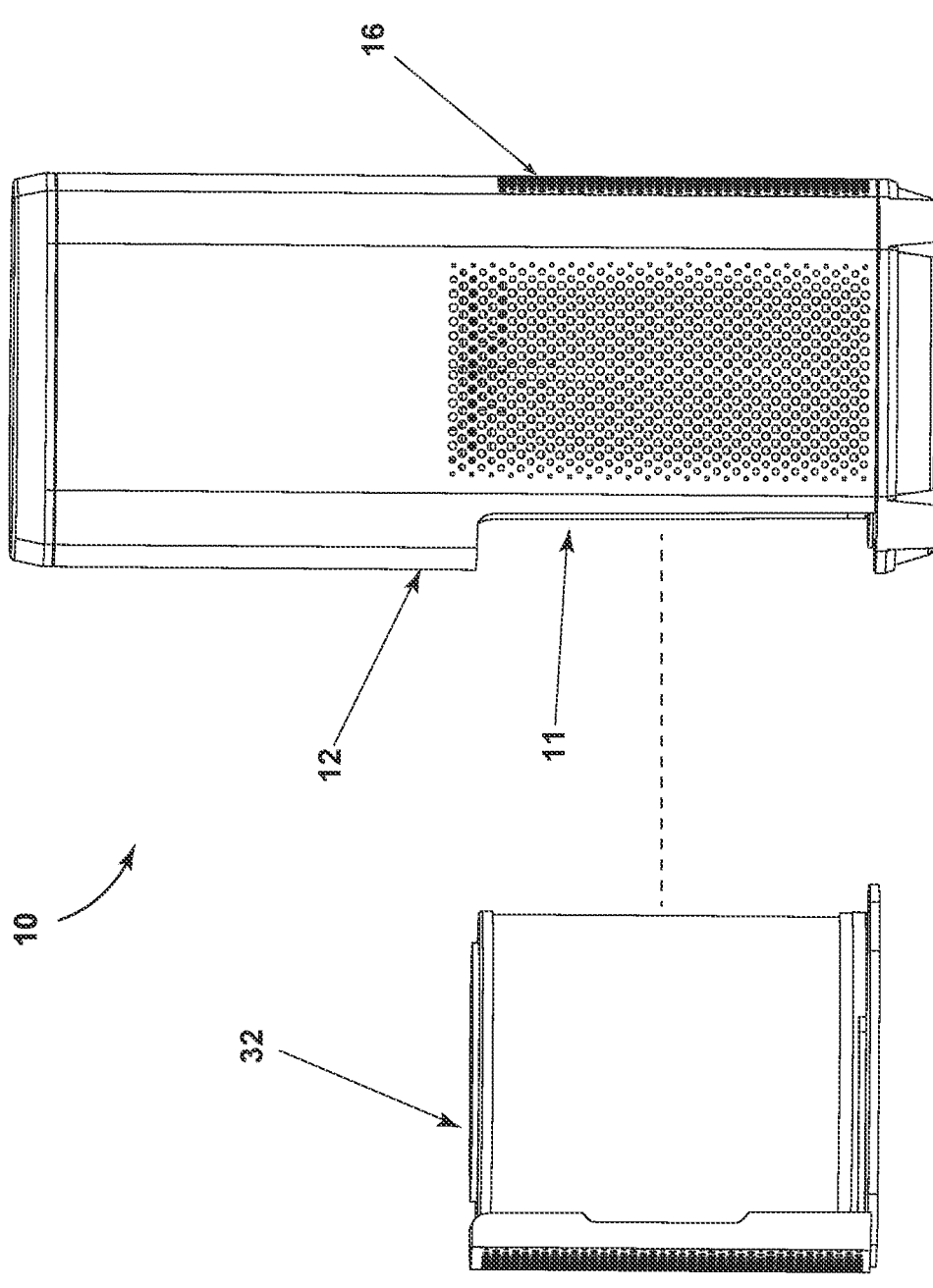
FIG. 2 is a side view of the air purifier of FIG. 1 with the closure assembly exploded from a remainder of the air purifier.

FIG. 2 is a side view of the air purifier 10, where the closure assembly 32 is removed from the lower portion 16 of the housing 12. That is, the closure assembly 32 is in the opened position defined by the second position relative to the housing 12. The closure assembly 32 is illustrated as a removable drawer, however, the closure assembly 32 can be one or more doors or other movable structures configured to open and close to provide access to at least a portion of the interior 11 of the housing 12.

Figure 3:
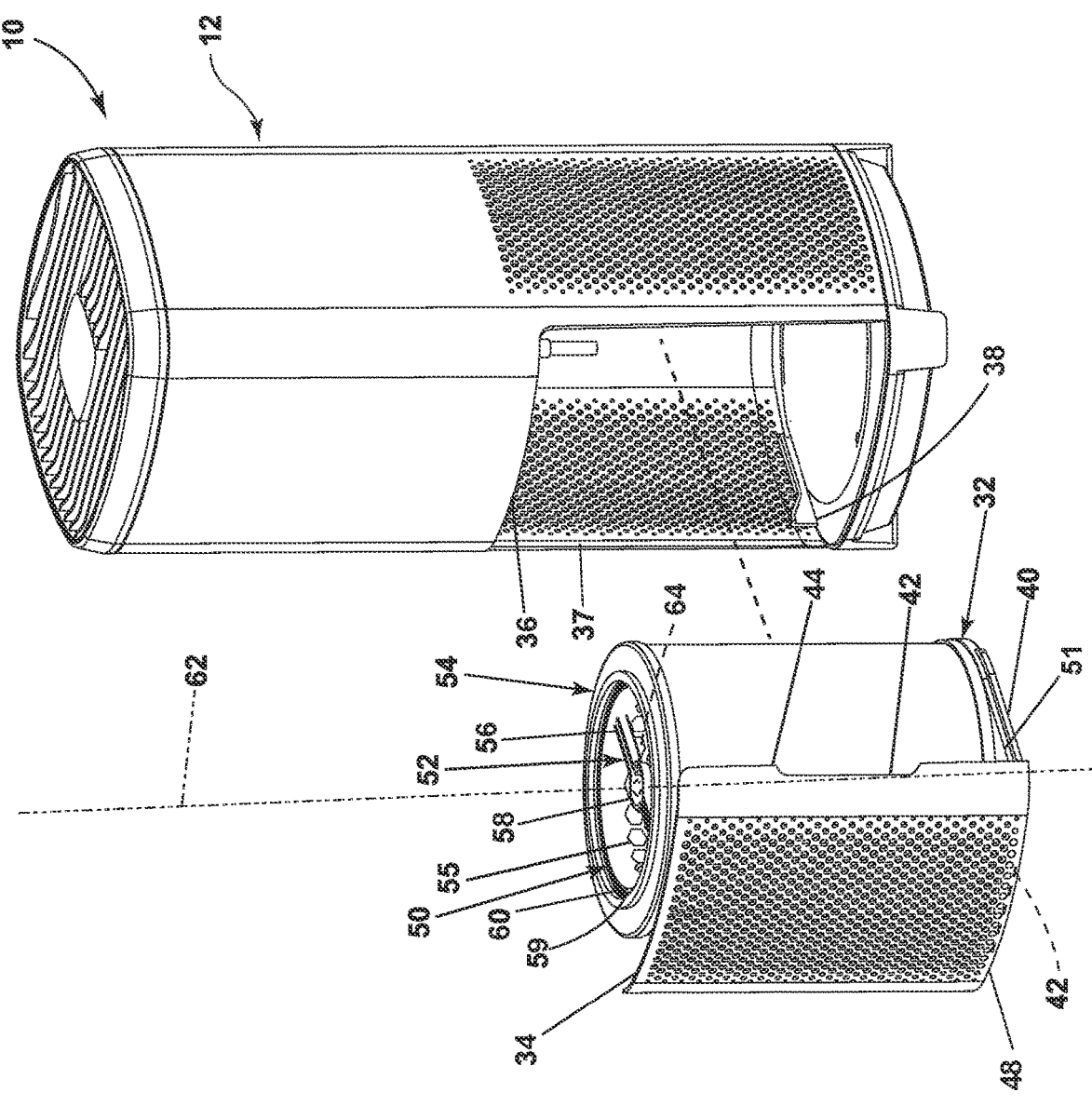
FIG. 3 is a perspective view of the air purifier of with the closure assembly exploded as in FIG. 2.

FIG. 3 further illustrates the closure assembly 32 of the air purifier 10 in the opened position defined by the second position. When in the opened position defined by the second position, the face 34 of the closure assembly 32 no longer closes to an edge 36 of the housing 12 that defines the opening 37. The closure assembly 32 can be slideably mounted to the housing 12 using any one or more combinations of a telescoping slide, an undermounted slide, a soft closing slide, a self-closing slide, or a ball bearing slide. As illustrated, by way of example, the closure assembly 32 can be slideably removed from the housing 12. A guide, bracket, or track 38 can be coupled to an interior portion of the housing 12. The track 38 can receive a protrusion, tongue, complimentary bracket, or arm 40 that is coupled to the closure assembly 32. The closure assembly 32 can at least partially close the opening 37 when in the closed position.

Optionally, the track 38 or arm 40 can include one or more stopping portions (not shown) that restrict the face 34 of the closure assembly 32 to extend a predetermined distance from the housing 12. It is further contemplated that the closure assembly 32 can be removed from the track 38 by a lifting motion, allowing a user to slide the closure assembly 32 to the predetermined distance and lift to remove the closure assembly 32 so that the closure assembly can extend beyond the predetermined distance or be fully removed from the housing 12.

A grasping portion, handle, or grip 42 can be formed in or adjacent to the face 34 of the closure assembly 32. As illustrated, by way of non-limiting example, the grip 42 is located on a side edge 44 of the face 34 of the closure assembly 32. Additionally, or alternatively, the grip 42 can be located at a lower edge 48 of the face 34. While illustrated as a recess or pocket it will be understood that the grip 42 can be any shaped or contoured recess or protrusion that allows a user to grasp and slide the closure assembly 32 away from or into the housing 12. It is contemplated that the closure assembly 32 can include a latching mechanism for retaining the closure assembly in the closed position defined by the first position. By way of non-limiting example, the latching mechanism can include a press latch in which the user presses the face 34 of the closure assembly 32 to release the closure assembly 32 from the housing 12. By way of further non-limiting example, the latching mechanism can include a magnetic closure element.

A filter mount or filter cage 50 can also be provided on the closure assembly 32. The filter cage 50 can be a unitary portion of the closure assembly 32. Alternatively, the filter cage 50 can be a separable component coupled to and part of the closure assembly 32. The filter cage 50 can extend upward or away from a closure base 51 of the closure assembly 32. The filter cage 50, as illustrated by way of example, is spaced from the face 34. A vertical axis 62 can be defined by the filter cage 50.

A plurality of filter cage perforations 55 can extend from an outside surface 59 to an inner surface 60. While the plurality of filter cage perforations 55 are illustrated as uniform hexagons, a variety of shapes and sizes are contemplated. A filter 54 can be provided with or operably coupled to the filter cage 50. By way of non-limiting example, the filter 54 can surround at least a portion of the filter cage 50 including, in the illustrated example, that the filter 54 can circumscribe the entire filter cage 50. It is contemplated that the filter 54 can be reusable or replaceable. While illustrated as cylinders, any shape filter or filter cage is contemplated. The vertical height of the filter 54 is greater than the vertical height of the filter cage 50. That is, when the filter 54 is mounted to the filter cage 50, the filter 54 can extend beyond the filter cage 50. Alternatively, it is contemplated that the filter 54 can have a height that is less than or equal to the filter cage 50. A filter gap can be defined as a space between the filter 54 and the face 34 when the filter 54 is coupled to the filter cage 50. Alternatively, one or more portions of the filter 54 can be in contact with one or more portions of the face 34 when the filter 54 is coupled to the filter cage 50.

A lighting system 52 can further be provided on the closure assembly 32. The lighting system 52, in a non-limiting example, can include at least one support beam 56 that supports a bulb mount 58. The at least one support beam 56 can be formed with or coupled to the filter cage 50, so that the at least one support beam 56 extends radially from the inner surface 60 of the filter cage 50. While illustrated as vertically above the plurality of filter cage perforations 55, the at least one support beam 56 can be vertically adjacent to or vertically below one of more filter cage perforations of the plurality of filter cage perforations 55. The at least one support beam 56 is illustrated as a single crossbar or support beam 56, however, any number beams are contemplated. The at least one support beam 56 can be positioned such that the bulb mount 58 is located along or at least partially aligns with the vertical axis 62 of the filter cage 50.

The bulb mount 58 or the at least one support beam 56 can include one or more electrical contacts 64 to provide power to a light source or bulb (not shown). Power can be provided to the one or more electrical contacts 64 directly from a housing electrical connection or via one or more electrical wires that extend from one or more portions of the closure assembly 32. By way of non-limiting example, one or more electrical contacts located at the arm 40, the face 34, the filter 54, the filter cage 50, or a bottom portion of the closure assembly 32 can receive power from one or more housing electrical connections. The power received from the one or more housing electrical connections can be transmitted via wires across the filter cage 50 and/or across one or more portions of the at least one support beam 56 to the one or more electrical contacts 64.

Power can be provided to the bulb when the closure assembly 32 is in the closed position as defined by the first position. Additionally, or alternatively, power can be provided to the bulb upon the detection of the proper position or location of the filter 54. Further, it is contemplated that the bulb can be provided with electrical power when the closure assembly 32 is in the closed position as defined by the first position and the filter 54 is detected as located in the proper position.

Figure 4:
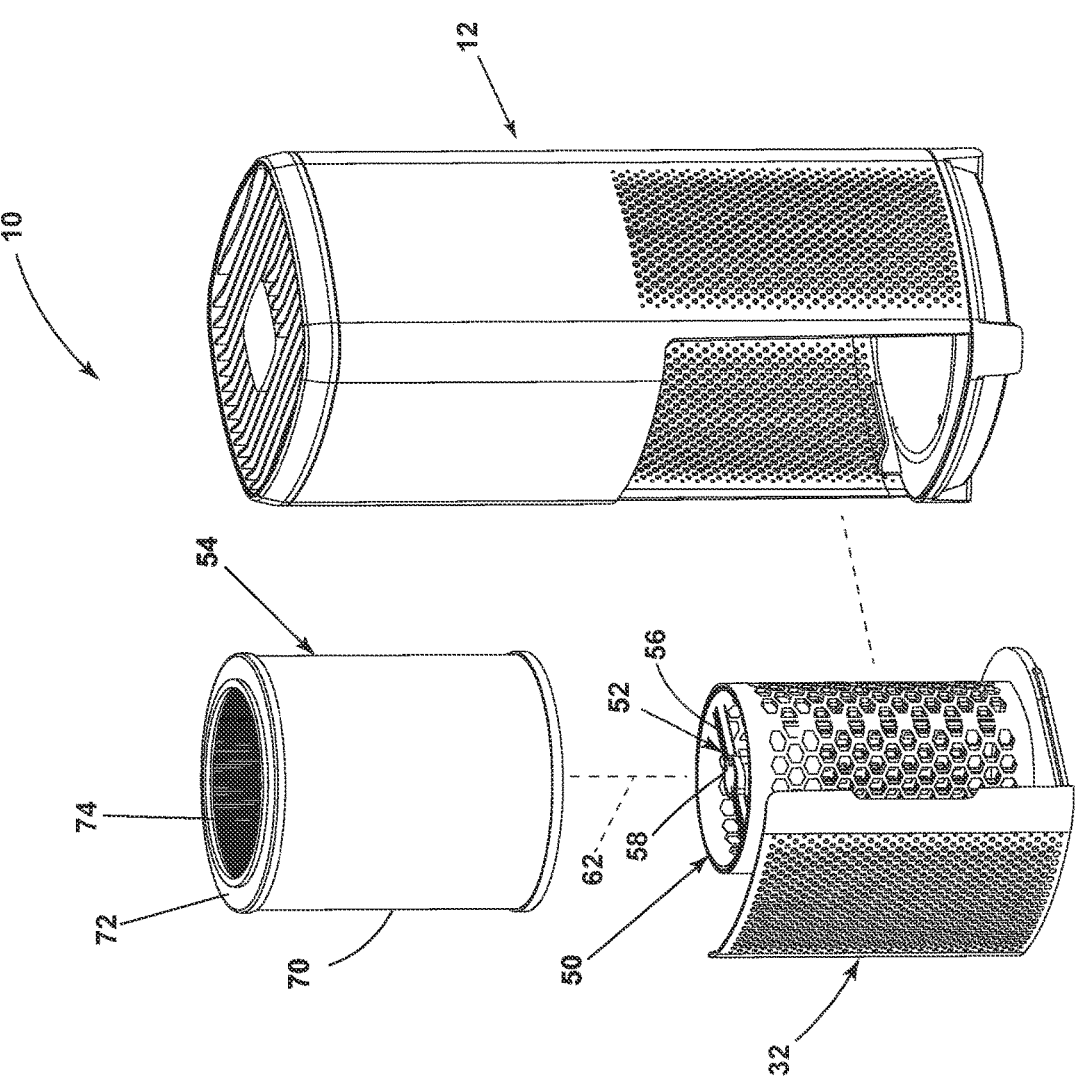
FIG. 4 is a perspective view of the air purifier of FIG. 2 with the closure assembly in an opened position defined by a second position, where a filter is exploded from the closure assembly.

FIG. 4 illustrates the filter 54 exploded from the filter cage 50. The filter 54, by way of example, is slidably removable from the filter cage 50. That is, a user can lift up on the filter 54 and it will slide over or off the filter cage 50. The filter 54 is illustrated as having three layers. The three layers of the filter 54 can be coupled together or formed and mounted as individual pieces. The outside layer 70 can be a non-woven pre-filter. The pre-filter can filter air or at least partially block light provided by the lighting system 52. The middle layer 72 can include a pleated filter. The pleated filter can be a High Efficiency Particulate Air (HEPA) filter. The inner layer 74 can be a carbon sponge. The carbon sponge can filter air or at least partially block light provided by the lighting system 52. It is contemplated that the filter 54 can be a flexible filter that is shipped in a compressed or flat arrangement. Additionally, or alternatively the filter 54 can be a framed filter. The frame of the filter can be configured to include electrical connections that can receive power from the housing 12. The frame of the filter 54 can include sensors that indicate the position or location of the filter 54 relative to the filter cage 50 or the position or location of the filter 54 relative to the housing 12.

Figure 5:
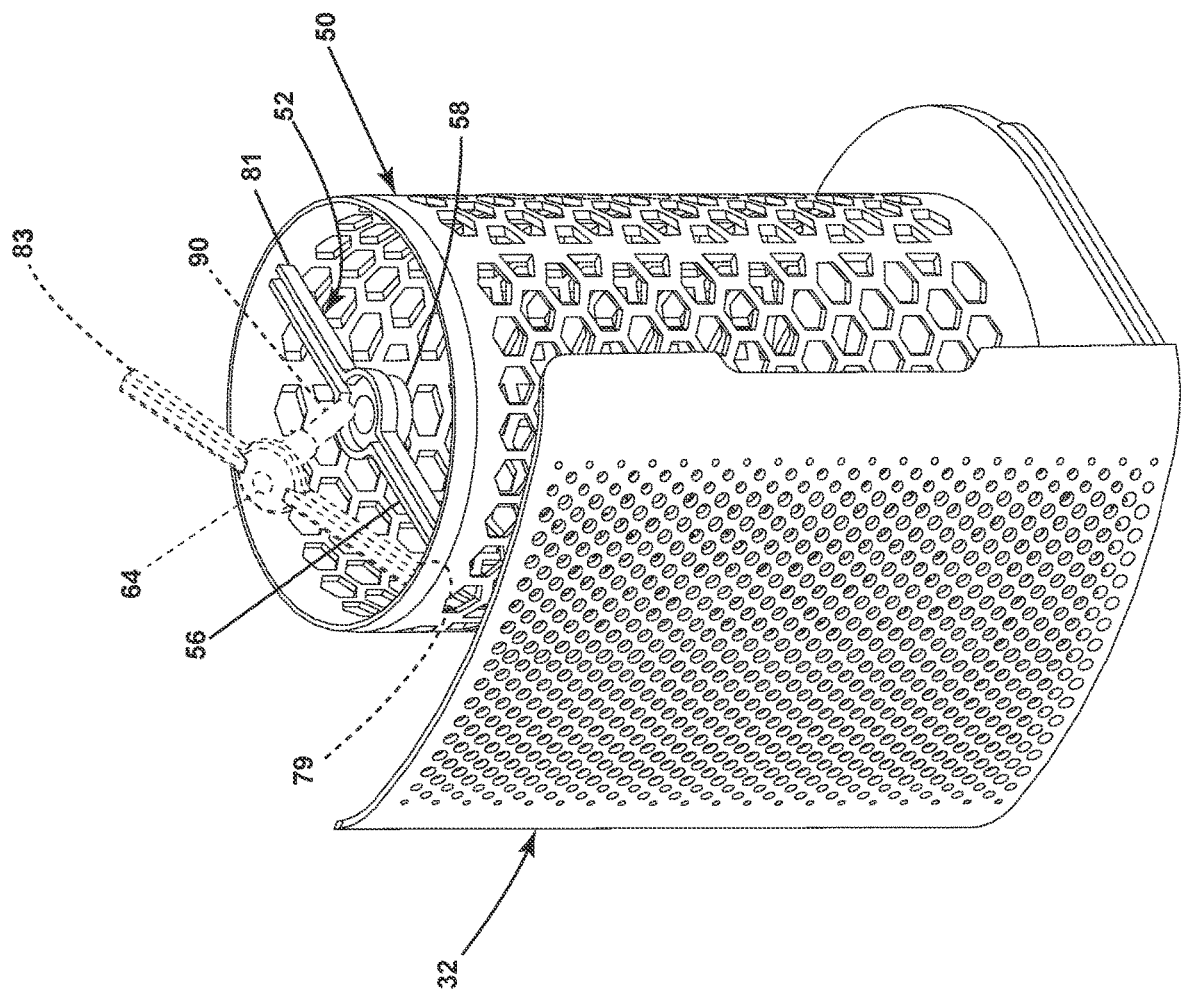
FIG. 5 is a perspective view of the closure assembly of FIG. 4.

FIG. 5 is a perspective view further illustrating the closure assembly 32. Optionally, a hinge 79 can be included at one or more portions of the at least one support beam 56. The hinge 79 can provide a space for electrical wires to pass from the filter cage 50 to the at least one support beam 56, providing power to the light source or bulb 90. The hinge 79 can allow the at least one support beam 56 to rotate into a position that allows a user to replace the bulb 90.

A locking portion 81 can selectively secure a rotatable end 83 of the at least one support beam 56. Alternatively, the electrical connection between wires at the filter cage 50 and wires running along the at least one support beam 56 can be at the locking portion 81.

Figure 6:
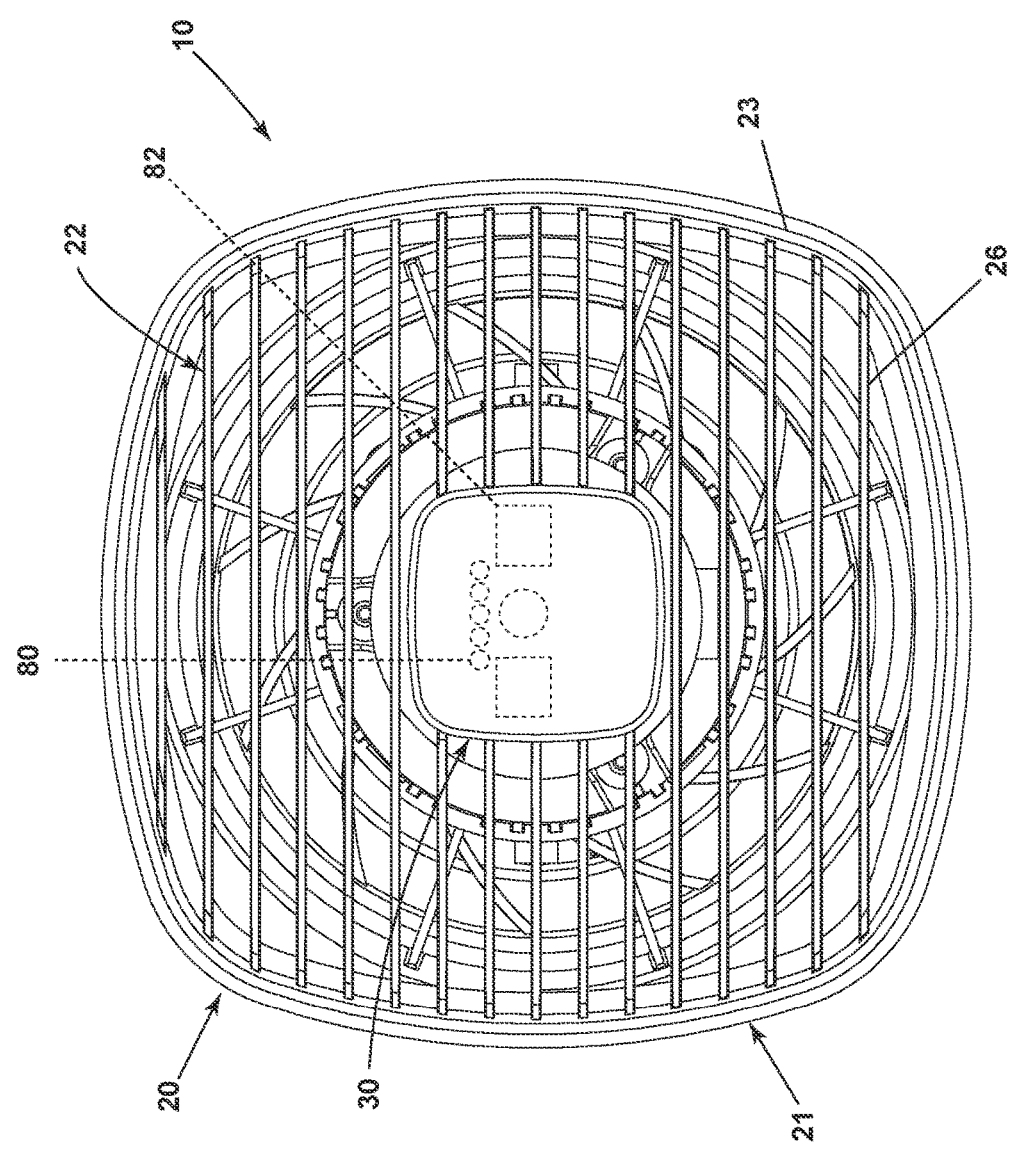
FIG. 6 is a top view of the air purifier of FIG. 1.

FIG. 6 is a top down view of the air purifier 10 further illustrating the user interface 30. The user interface 30 can include or couple to a controller (not shown). While the user interface 30 is illustrated as centrally located in the plurality of flow divertors 26 of the vent 22, it is contemplated that the user interface 30 can be located in any position at or adjacent the top portion 20. It is further contemplated that the user interface 30 can be located on any one or more portions of the air purifier 10, as one or more user interfaces are contemplated.

The user interface 30 can include indicator lights 80. The indicator lights 80 can provide information about the air purifier 10 to the user. Information provided to the user by the indicator lights 80 can include, but is not limited to, a fan speed, a position of the closure assembly 32, activation or deactivation of the light system 52, filter status, blub status, or activation or duration of a timer. The user interface 30 can include one or more buttons 82 that adjust one or more settings or monitor the status of one or more components of the air purifier 10. The one or more buttons 82 can be one or more capacitive touch buttons or screens. Additionally, or alternatively, the one or more buttons 82 can include one or more mechanical switches. The one or more buttons 82 can, by way of non-limiting example, turn on or provide power to the air purifier 10, change the fan speed, the activation or deactivation of the bulb of the light system 52, set a timer indicative of how long the user wishes the air purifier 10 to operate before automatically shutting off, lock or unlock a latching assembly that allows the closure assembly 32 to be moved from the closed position defined by the first position to the opened position defined by the second position or secure the closure assembly 32 in the first position, check the status of the bulb, or check the status of the filter 54 or one or more layers of the filter. It is contemplated that each of the at least one or more buttons can have a different size or shape. Shapes of the at least one button can include, but not limited to, circles, rectangles, squircles, rounded rectangles, triangles, ovals, hexagons. Optionally, the indicator lights 80 can circumscribe or otherwise be adjacent to or included with the one or more buttons 82.

Figure 7:
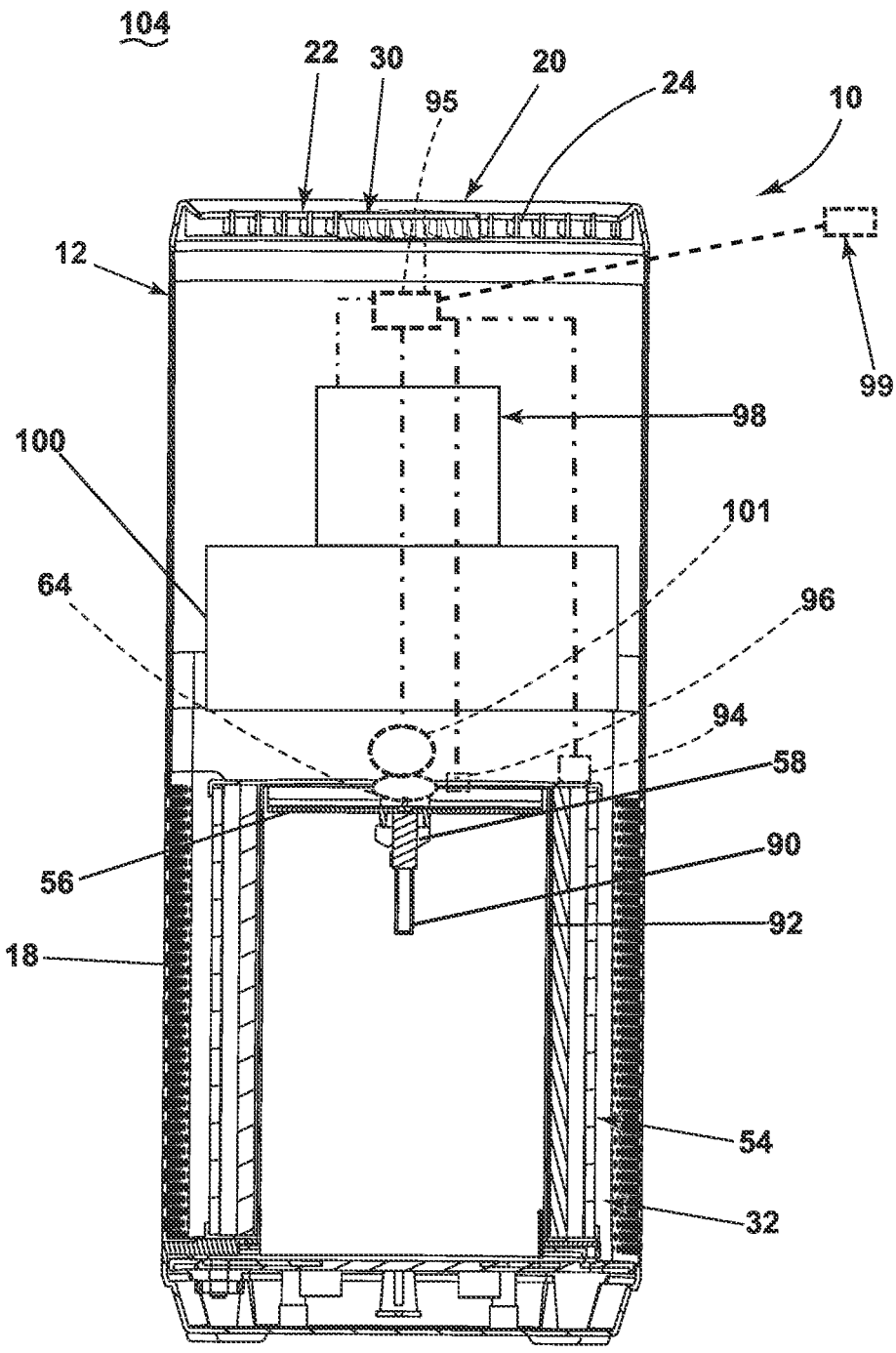
FIG. 7 is a schematic cross section view of the air purifier of FIG. 1 according to various aspects described herein.

FIG. 7 is a schematic cross-sectional view of the air purifier 10 when the closure assembly 32 is in the closed position as defined by the first position. A motor assembly 98 can be located within the interior of the housing 12. The motor assembly 98 can provide output to drive a fan 100 within the interior of the housing 12 when electrical power is provided to the motor assembly 98. Optionally, a controller 95 can be in electrical communication with the motor assembly 98.

A power supply 99 can be electrically coupled or included in the air purifier 10. The power supply 99 can be an external power supply, such as, but no limited to, a household power supply having providing approximately 120 volts and alternating current when the circuit is closed. Alternatively, the power supply 99 can be a battery pack or circuit coupled to any voltage supply that can provide either direct current or alternating current. It is further contemplated that the power supply 99 can be within the housing 12, such as a battery pack or other portable device that provides the required electrical power. Optionally, the power supply can be in electrical communication with a circuit or the controller 95.

The user interface 30 can be in communication with the controller 95. Additionally, or alternatively, the user interface 30 can receive power from the power supply 99.

A bulb 90 can be suspended within the filter cage 50 by the at least one support beam 56. The bulb 90 can extend downward from the bulb mount 58. The bulb 90 can be one or more of an ultraviolet light such as an ultraviolet germicidal irradiation (UVGI) or an ultraviolet C (UV-C). UVGI and UV-C are short-wavelength ultraviolet radiation that can kill or inactivate pathogens or microorganisms. One way in which the UVGI and UV-C kill or inactivate pathogens or microorganisms is by destroying nucleic acids and disrupting DNA, which can leave the pathogens or microorganisms unable to perform vital cellular functions. UVGI and UV-C are ultraviolet radiation with wavelengths typically between 200 and 290 nm.

During operation, the bulb 90 provides ultraviolet light in a downward and radially outward direction. The ultraviolet light from the bulb 90 can kill or disable pathogens or microorganisms that can be present in the air within the filter cage 50. Additionally, the ultraviolet light from the bulb 90 can kill or disable pathogens or microorganisms present within the filter 54. By way of non-limiting example, the ultraviolet light from the bulb 90 can kill or disable pathogens and microorganisms on an inner surface 92 of the inner layer 74 that is exposed to the ultraviolet light of the bulb 90 although it is contemplated that the multilayer filter 54 can be formed such that the ultraviolet light can penetrate into further layers of the filter 54. The filter cage 50 includes a plurality of filter cage perforations 55 to allow the ultraviolet light from the bulb 90 to reach the filter 54 while the filter 54 is mounted to the filter cage 50.

A first sensor 94 can be located in the interior of the housing 12. While illustrated as being coupled to a side portion of the housing 12, it is contemplated that the first sensor 94 can be suspended or otherwise positioned in a location spaced from the side portion of the housing 12. The first sensor 94 can detect or provide a signal indicative of the presence, the position, or the location of the filter 54. The first sensor 94 can be in electrical communication with a circuit or controller 95. That is, the first sensor 94 can send an electrical signal to the controller 95 to close a break in a circuit, or the first sensor 94 can directly close a break in the circuit when the filter 54 is properly located within the housing 12.

Alternatively, the first sensor 94 can be mounted to the closure assembly 32 and brought into communication with the controller 95 when contact between the closure assembly 32 and the housing 12 are achieved. That is, the position or the location of the filter 54, as detected by the first sensor 94, can also indicate that the closure assembly 32 is in the closed position defined by the first position.

A second sensor 96 can be located in the interior of the housing 12. While illustrated as being coupled to a side portion of the housing 12, it is contemplated that the second sensor 96 can be suspended or otherwise positioned in a location spaced from the side portion of the housing 12. The second sensor 96 can detect or provide a signal indicative of the position of the lighting system 52. The second sensor 96 can be in electrical communication with the controller 95 to close a break in the circuit, or the second sensor 96 can directly close a break in the circuit when the lighting system 52 is properly located within the housing 12. When the lighting system 52 is detected in the correct location by the second sensor 96, the closure assembly 32 is in the closed position defined by the first position.

While illustrated as the first sensor 94 and the second sensor 96, any number of sensors are contemplated. Sensors can include, but are not limited to, a spring leaf switch or other mechanical switch, an optical or fiber-optic sensor, potentiometric, eddy current-based, capacitive, or inductive position sensor. At least one housing electrical connection 101 is coupled to the housing 12 and is located above the lighting system 52 of the closure assembly 32 when the closure assembly 32 is in the closed position defined by the first position. The at least one housing electrical connection 101 can be in electrical communication with the circuit or the controller 95. When the closure assembly 32 is in the closed position defined by the first position, the at least one housing electrical connection 101 can provide electrical power to the one or more electrical contacts 64 of the lighting system 52.

Alternatively, the at least one housing electrical connection 101 can be located anywhere within the housing 12 such that power can be provided to the bulb 90. For example, wherein when the first sensor 94 or the second sensor 96 provides an output indicative of the filter 54 or the closure assembly 32 in the first filter position or the closure assembly 32 in the closed position, electrical power can flow from the housing 12 via the at least one housing electrical connection 101 to one or more wires located at or along the filter 54 or filter cage 50. These wires can optionally couple to one or more wires that span at least a portion of the at least one support beam 56 to provide power to the bulb mount 58, the one or more electrical contacts 64 of the lighting system 52, or the bulb 90.

Figure 8:
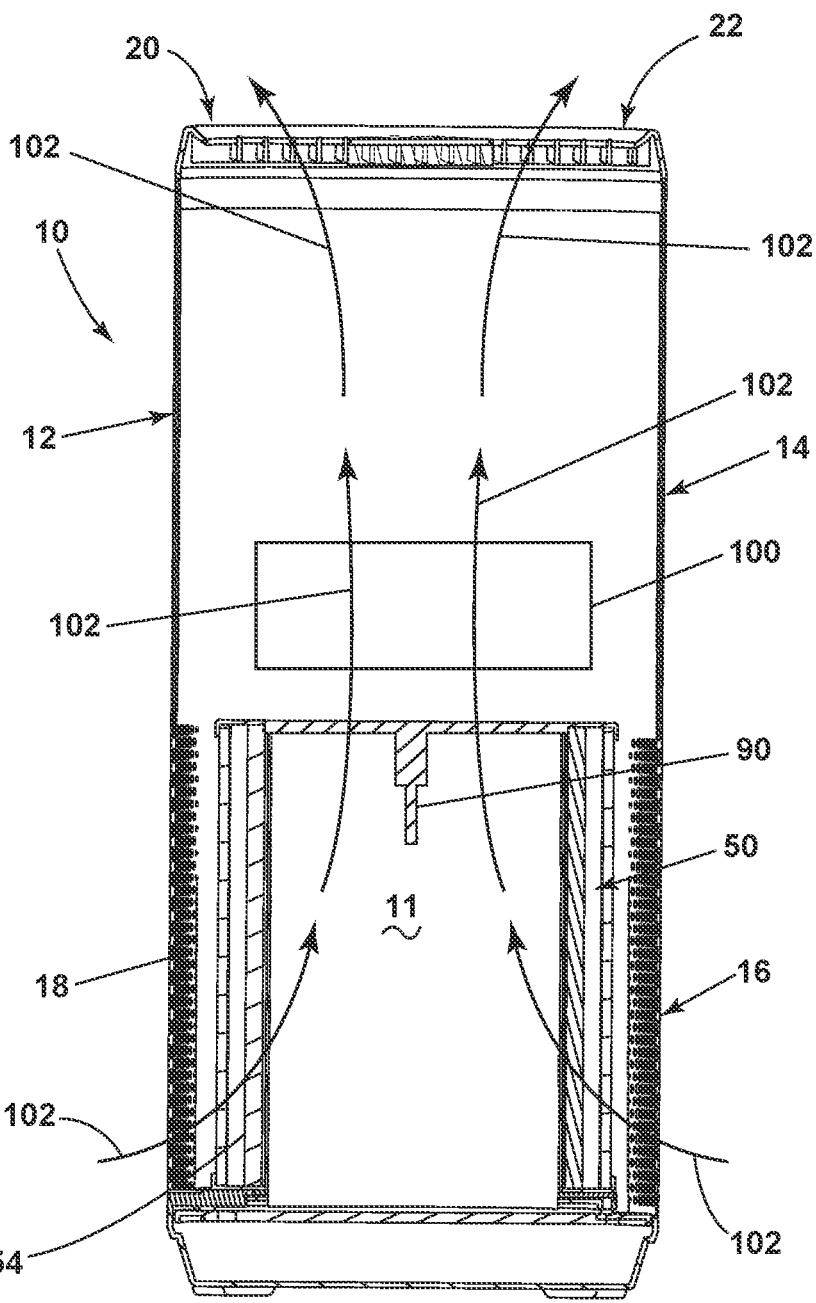
FIG. 8 is a schematic view of the air purifier of FIG. 1 illustrating an air flow according to various aspects described herein.

FIG. 8 is a schematic view of the air purifier 10 illustrating an air flow 102. The fan 100 draws air into the interior 11 of the air purifier 10 through the plurality of perforations 18 in the lower portion 16 of the housing 12. The air flow 102 then passes through the filter 54 and into the filter cage 50. The air flow 102 can be filtered or otherwise purified as it passes through the filter 54. Further, the ultraviolet light from the bulb 90 can kill or disable pathogens or microorganisms that may be present in the air flow 102. The filtered, purified, or otherwise cleaner air flow 102 then passes upward through the fan 100 into the upper portion 14 of the housing 12. The air flow 102 exits the interior 11 of the air purifier 10 through the vent 22 in the top portion 20 of the housing 12.

In operation, the air purifier 10 is coupled to the power supply 99. A user initiates the air purifier 10 via the user interface 30 or a cellular device. Upon determining that the closure assembly 32 is in the closed position defined by the first position via the first sensor 94 and the second sensor 96, electrical power from the power supply 99 is allowed to be supplied to the motor assembly 98 and to the lighting system 52. That is, if the closure assembly 32 is in any other position than the closed position defined by the first position, or if the filter 54 is missing or misplaced, the motor assembly 98 or the lighting system 52 do not receive electrical power. In other words, the lighting system 52 or the motor assembly 98 are selectively electrified, and only provided with electrical power when the closure assembly 32 is fully inserted into the housing 12.

Optionally, an error message or indicator light 80 can communicate to a user if the closure assembly 32 is not in the closed position defined by the first position or the filter 54 has not been mounted or is improperly mounted on the filter cage 50.

When electrical power is provided to the motor assembly 98, the motor assembly 98 drives the fan 100.

Electrical power is provided to the lighting system 52 via the at least one housing electrical connection 101 when the closure assembly 32 is in the closed position defined by the first position. Electrical power passes from the at least one housing electrical connection 101 to the one or more electrical contacts 64 of the lighting system 52 located below the at least one housing electrical connection 101. The electrical power passes from the one or more electrical contacts 64 to the bulb 90 via the bulb mount 58. The bulb 90, upon activation by the electrical power, provides UV-C or UVGI to filtered air within the filter cage 50.

The fan 100, when activated, can result in an air flow illustrated by arrows 102. The air flow includes air from an exterior 104 of the air purifier 10 that is drawn into the interior 11 of the housing 12 through the plurality of perforations 18. Once the air passes through the through the plurality of perforations 18, the air flows through the three layers 70, 72, 74 of the filter 54 to clean or filter the air. The filter 54 removes particles from the air. The particles removed from the air can have a dimension that is greater than or equal to 0.3 micrometer (micron). The clean or filtered air then enters the filter cage 50 via the plurality of filter cage perforations 55. The bulb 90, when activated, can provide ultraviolet light in a downward or radially outward direction to kill or disable pathogens or microorganisms that can be present in the filtered air within the filter cage 50 to purify the air. The ultraviolet light from the bulb 90 can pass through the filter cage 50 via the filter cage perforations 55 to purify or otherwise clean the filter 54.

The clean and purified air is then drawn from the filter cage 50 into the upper portion 14 of the housing 12 via the fan 100. The clean and purified air exits the upper portion 14 of the air purifier 10 through the plurality of openings 24 of the vent 22 in the top portion 20 of the housing 12.

When the bulb 90 or the filter 54 need to be replaced, the user can quickly remove electrical power to the motor assembly 98 and the bulb 90 by moving the closure assembly 32 from the closed position defined by the first position to the opened position defined by the second position. Alternatively, the user can make appropriate selections via the user interface to remove electrical power from the motor assembly 98 or the bulb 90. In the opened position defined by the second position, the filter 54 and bulb 90 are easily accessible. The filter 54 can be slideably removed from the filter cage 50. Additionally, or alternatively, the user can easily reach into the filter cage 50 to remove or replace the bulb 90, as the bulb 90 and the bulb mount 58 are located at an upper central location of the filter cage 50.

Aspects of the present disclosure provide for a variety of benefits, including the lighting system that provides UV-C or UVGI to filtered air within the filter mount. The suspension of the bulb into the filter mount allows for ultraviolet light to provide 360 degrees of ultraviolet light to air in the filter mount. The large volume of the filter mount and the 360-degree radial output of ultraviolet light kills or disables a significant number of pathogens prior to the air exiting the air purifier.

The bulb extending into the filter cage increases the UV-C or UVGI exposure to an increased surface area of filter. That is, the bulb extending into the filter cage can provide ultraviolet light to the air within the filter cage as well as the filter. This allows for germs, bacteria, viruses, or mold that are present in the air or on the inner surface of the filter to be killed by the ultraviolet light provided by the suspended bulb.

The suspended bulb is easier to replace than bulbs located in an inner cavity or beneath filters.

The removable drawer or closure assembly that unitarily includes the filter mount and bulb mount coupled to the filter cage provide an ease of replacement of the filter, bulb, or both. The mounting of the bulb to the at least one support beam extending from at least a portion of the filter cage allows for easier access to change the bulb.

Unlike traditional air purifiers where the entire housing is inverted to access the filter and/or bulb, the closure assembly or drawer feature as disclosed herein allows access to the filter and/or the bulb while the housing remains upright. Therefore, the closure assembly, as described improves access for users. The closure assembly also improves safety, as there is no reason for the user to invert the ultraviolet bulb.

The sensors for the closure assembly ensure that power is not provided to the lighting system unless the lighting system is properly located within the housing. Further, power is not provided to the lighting system or motor assembly if the filter is missing or not mounted properly. The air purifier, as disclosed, prevents a user from unintentional exposure to ultraviolet light from the bulb when the removable drawer or the closure assembly is moved from the closed position to the opened position or via versa.

The filter cage mounted to or formed as part of the removable drawer or closure assembly can support the filter. A benefit of this arrangement is that the filter does not require a frame or other structural support, as the structural and shape support is provided by the filter cage. This allows the filters to be packaged as a flat filter or folded float filter.

While the invention has been specifically described in connection with certain specific embodiments thereof, it is to be understood that this is by way of illustration and not of limitation. Reasonable variation and modification are possible with the scope of the foregoing disclosure and drawings without departing from the spirit of the invention which, is defined in the appended claims. Hence, specific dimensions and other physical characteristics relating to the embodiments disclosed herein are not to be considered as limiting, unless the claims expressly state otherwise.

Further aspects of the disclosure are provided by the subject matter of the following clauses:

An air purifier, comprising a housing defining an interior, the housing having an opening, a closure assembly selectively moveable between a closed position and an opened position, wherein the closure assembly in the closed position at least partially closes the opening, the closure assembly further comprising a filter mount, and a bulb mount configured to retain a light source and wherein power is unavailable to the light source if the closure assembly is in an at least partially opened position.

The air purifier of the previous clause, wherein the filter mount defines a vertical axis and the bulb mount is at least partially aligned with the vertical axis.

The air purifier of any of the preceding clauses, wherein the closure assembly is a drawer selectively removable from the housing.

The air purifier of any of the preceding clauses, wherein the filter mount extends upward or away from a closure base of the closure assembly.

The air purifier of any of the preceding clauses, wherein the air purifier is a standalone air purifier.

The air purifier of any of the preceding clauses, further comprising a set of legs or feet located at a bottom portion of the housing.

The air purifier of any of the preceding clauses, wherein the light source is an ultraviolet light.

The air purifier of any of the preceding clauses, wherein the ultraviolet light is ultraviolet germicidal irradiation (UVGI) or ultraviolet C (UV-C).

The air purifier of any of the preceding clauses, further comprising a sensor located in the interior of the housing.

The air purifier of any of the preceding clauses, further comprising a filter removably mounted to the filter mount, wherein the sensor provides a signal indicative of the position of the filter.

The air purifier of any of the preceding clauses, wherein the sensor detects or provides a signal indicative of the closed position or the opened position of the closure assembly.

The air purifier of any of the preceding clauses, wherein power is provided to the light source when the sensor provides a signal indicative of the closure assembly in the closed position.

The air purifier of any of the preceding clauses, wherein the sensor is a first sensor and a second sensor, wherein the first sensor detects or provides a signal indicative of the position of a filter and the second sensor detects or provides a signal indicative of the closed position or the opened position of the closure assembly.

The air purifier of any of the preceding clauses, wherein the housing includes an upper portion and a lower portion and wherein the closure assembly is located in the lower portion.

The air purifier of any of the preceding clauses, wherein the upper portion includes a top portion having a vent with a plurality of flow divertors defining a plurality of openings therebetween.

The air purifier of any of the preceding clauses, further comprising a user interface located on one or more portions of the housing.

The air purifier of any of the preceding clauses, wherein the user interface is located on a top portion of the housing.

The air purifier of any of the preceding clauses, wherein the closure assembly slideably mounts to the housing using any one or more of a telescoping slide, an undermounted slide, a soft closing slide, a self-closing slide, or a ball bearing slide.

The air purifier of any of the preceding clauses, wherein the closure assembly further comprises a grasping portion, handle, or grip formed in a face of the closure assembly.

The air purifier of any of the preceding clauses, wherein the housing is a prism having a base or cross-sectional shape that is a squircle, circle, square, rounded rectangle, oval, or ellipse.

What is claimed is:

1. An air purifier, comprising:
   a housing defining an interior, the housing having an opening; and
   a closure assembly selectively moveable between a closed position and an opened position, wherein the closure assembly in the closed position at least partially closes the opening, the closure assembly further comprising:
   a filter mount;
   a bulb mount configured to retain a light source; and
   a support beam supporting the bulb mount and extending radially from an inner surface of the filter mount; and
   wherein power is unavailable to the light source if the closure assembly is in an at least partially opened position.

2. The air purifier of claim 1, wherein the filter mount defines a vertical axis and the bulb mount is at least partially aligned with the vertical axis; and
   wherein one or more electrical wires are disposed along the support beam.

3. The air purifier of claim 1, wherein the closure assembly is a drawer selectively removable from the housing.

4. The air purifier of claim 1, wherein the filter mount extends upward or away from a closure base of the closure assembly;

wherein the filter mount includes a plurality of perforations; and wherein the support beam is vertically above the plurality of perforations.

5. The air purifier of claim 1, further comprising a set of legs or feet located at a bottom portion of the housing.

6. The air purifier of claim 1, wherein the light source is an ultraviolet light, and wherein the ultraviolet light is ultraviolet germicidal irradiation (UVGI) or ultraviolet C (UV-C).

7. The air purifier of claim 1, further comprising a sensor located in the interior of the housing.

8. The air purifier of claim 7, further comprising a filter removably mounted to the filter mount, wherein the sensor provides a signal indicative of the position of the filter relative to the filter mount.

9. The air purifier of claim 7, wherein the sensor detects or provides a signal indicative of the closed position or the opened position of the closure assembly.

10. The air purifier of claim 9, wherein the power is provided to the light source when the sensor provides the signal indicative of the closure assembly in the closed position.

11. The air purifier of claim 7, wherein the sensor is a first sensor and a second sensor, wherein the first sensor detects or provides a signal indicative of the position of a filter relative to the filter mount and the second sensor detects or provides a signal indicative of the closed position or the opened position of the closure assembly.

12. The air purifier of claim 1, wherein the housing includes an upper portion and a lower portion and wherein the closure assembly is located in the lower portion, and wherein the upper portion includes a top portion having a vent with a plurality of flow divertors defining a plurality of openings therebetween.

13. The air purifier of claim 1, wherein the closure assembly slideably mounts to the housing using any one or more of a telescoping slide, an undermounted slide, a soft closing slide, a self-closing slide, or a ball bearing slide.

14. The air purifier of claim 1, wherein the housing is a prism having a base or cross-sectional shape that is a squircle, circle, square, rounded rectangle, oval, or ellipse.

15. An air purifier, comprising:

a housing defining an interior, the housing having an opening;

a power supply electrically coupled to the housing to provide power thereto; and a closure assembly selectively moveable between a closed position and an opened position, wherein the closure assembly in the closed position at least partially closes the opening, the closure assembly comprising:

a filter mount;

a bulb mount configured to retain a light source; and a support beam supporting the bulb mount and extending radially from an inner surface of the filter mount;

wherein the power is provided to the light source when the closure assembly is in the closed position.

16. The air purifier of claim 15, wherein the power is provided from the housing to the light source via the closure assembly when the closure assembly is in the closed position.

17. The air purifier of claim 15, further comprising one or more electrical contacts for electrically coupling the light source to one or more electrical wires that extend from one or more portions of the closure assembly.

18. An air purifier, comprising:

a housing defining an interior, the housing defining an opening;

a power supply electrically coupled to the housing to provide power thereto; and a closure assembly selectively moveable between a closed position and an opened position, wherein the closure assembly in the closed position at least partially closes the opening, the closure assembly comprising:

a filter mount;

a filter removably mounted to the filter mount;

a bulb mount configured to retain a light source; and a support beam supporting the bulb mount and extending radially from an inner surface of the filter mount; and wherein the power is provided to the light source through the closure assembly when at least one of the closure assembly is in the closed position or the filter is located in a predetermined position relative to the filter mount.

19. The air purifier of claim 18, wherein the filter mount defines a vertical axis and the light source is at least partially aligned with the vertical axis;

wherein the filter circumscribes the filter mount.

20. The air purifier of claim 19, wherein the light source is mounted to the support beam, and wherein electrical wires pass from the filter mount to the light source via at least one support beam.

* * * * *